United States Patent [19]

Kaufhold

[11] Patent Number: 4,778,920

[45] Date of Patent: Oct. 18, 1988

[54] PROCESS FOR THE PRODUCTION OF CHLORINE-FREE CYCLOPROPANECARBOXYLIC ACID ESTERS

[75] Inventor: Manfred Kaufhold, Marl, Fed. Rep. of Germany

[73] Assignee: Huels Aktiengesellschaft, Marl, Fed. Rep. of Germany

[21] Appl. No.: 922,902

[22] Filed: Oct. 24, 1986

[30] Foreign Application Priority Data

Oct. 26, 1985 [DE] Fed. Rep. of Germany ....... 3538133

[51] Int. Cl.$^4$ .............................................. C07C 69/74
[52] U.S. Cl. .................................... 560/124; 560/226
[58] Field of Search ................................ 560/124, 226

[56] References Cited

U.S. PATENT DOCUMENTS

| | | | |
|---|---|---|---|
| 2,992,269 | 7/1961 | Horrom | 560/124 |
| 3,077,496 | 2/1963 | Julia | 560/124 |
| 3,123,629 | 3/1964 | Julia | 560/124 |
| 3,711,549 | 1/1973 | Phillips | 564/134 |
| 3,995,054 | 11/1976 | Henrick | 424/305 |
| 4,217,300 | 8/1980 | Lantzsch | 560/124 |
| 4,310,464 | 1/1982 | Costain | 560/124 |
| 4,520,209 | 5/1985 | Schwarze | 560/124 |
| 4,590,292 | 5/1986 | Blackwell | 560/124 |

FOREIGN PATENT DOCUMENTS

2751134 5/1979 Fed. Rep. of Germany .
2941211 5/1981 Fed. Rep. of Germany .
2008111 5/1979 United Kingdom .

OTHER PUBLICATIONS

Bunce, Organic Preparations and Procedures, Int. 6, pp. 193–196 (1974).
Reppe, Annalen der Chemie, 596, pp. 163–224 (1955).
"Pharmazeutische Wirkstoffe", pp. 619, 227–228 and 747–748, Kleenan, V. A. (1982).

*Primary Examiner*—Michael L. Shippen
*Attorney, Agent, or Firm*—Millen & White

[57] ABSTRACT

For the production of chlorine-free cyclopropanecarboxylic acid esters, gamma-butyrolactone and butanol are reacted, in a first step, with hydrogen chloride in the absence of a catalyst at a temperature of 120°–140° C., the resultant gamma-chlorobutyric acid butyl ester is cyclized at 100°–200° C. with a solution of a sodium alcoholate in the corresponding alcohol of 4 or more carbon atoms and this product is optionally interestified in a third step with a higher-boiling alcohol of more than 4 carbon atoms. The second and third steps can be performed in one step, if desired.

18 Claims, No Drawings

PROCESS FOR THE PRODUCTION OF CHLORINE-FREE CYCLOPROPANECARBOXYLIC ACID ESTERS

BACKGROUND OF THE INVENTION

The invention relates to a process for the production of chlorine-free cyclopropanecarboxylic acid esters of Formula 1 by reacting gamma-butyrolactone with hydrogen chloride and a butyl alcohol to form a gamma-chlorobutyric acid ester 2 and subsequent cyclization with an alcoholate to 1, well as interesterification of 1 to a higher-boiling ester 3.

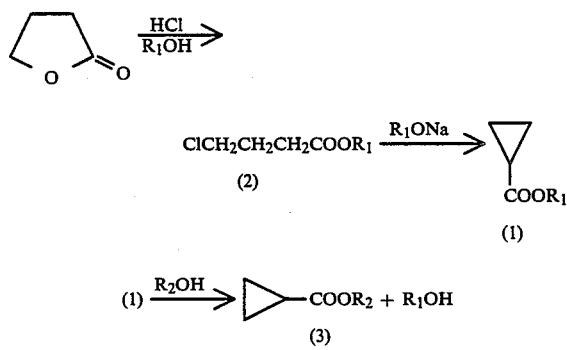

Syntheses of gamma-chlorobutyric acid esters and cyclopropanecarboxylic acid ester, starting with the readily accessible gammaa-butyrolactone, have been known from the literature.

In his article, Reppe described (Reppe, Annalen der Chemie 596: 163–224[1955]) the synthesis of gamma-chlorobutyric acid methyl, ethyl, propyl and butyl esters as a single-step process of introducing hydrogen chloride into a solution of gamma-butyrolactone and the corresponding alcohol, using zinc chloride as the catalyst. Due to the formation of high-boiling compounds, by a secondary reaction, Reppe achieved only low yields, for example, 50.4% in case of the methyl ester.

Therefore, a process to produce cyclopropanecarboxylic acid esters has been suggested in DOS No. 2,751,134, operating at low temperatures of 0°–20° C. and with thionyl chloride in place of hydrogen chloride. The yield of methyl ester, 91.3%, is relatively high. However, this process has 2 drawbacks: the high price thionyl chloride and the formation of gaseous sulfur dioxide during the reaction. This latter gas must be destroyed or removed by expensive technical measures for reasons of environmental protection.

Several of strong alkaline compounds have been proposed for the cyclization of gamma-chlorobutyric acid ester; for example, sodium amide (U.S. Pat. No. 3,294,833), sodium methylate in toluene DOS No. 1,939,759 and DOS No. 2,751,133), sodium tert amylate (M. and S. Julia et al., Bull. Soc. Chim. Fr. 1960 No. 2: 304–312) and sodium methylate in methanol (German Pat. No. 2,941,211).

The last-mentioned patent, wherein additional literature references are cited and discussed, contains the statement that industrially interesting yields can only be obtained by using, as the condensation agent, sodium hydride, sodium amide or alcohol-free alcoholates. The presence of alcohols leads to secondary reactions. In the cyclization of gamma-chlorobutyric acid ethyl ester with sodium methylate in ethanol, the 4-ethoxy-butyric acid ethyl ester is formed as a by-product by substitution. The analogous problem is said to occur when using the reseective methyl compounds.

The process of German Pat. No. 2,941,211 solves the problem of yield when employing the methyl and ethyl esters, by applying high temperatures—in a temperature range of 90°–200° C.—and by the utilization of superatmospheric pressure.

This temperature range, in the system of gamma-chlorobutyric acid ethyl ester, sodium amylate in tertamyl alcohol, leads, as demonstrated by Julia et al. (see above), to yields of only 45% of theory. Accordingly, a clear teaching can be gleaned from the totality of the literature citations that the presence of alcohols represents a disturbing factor in cyclization—except for the use of the systems of sodium ethylate in ethanol and sodium methylate in methanol at tempeatures at 90°–200° C.

However, these two systems have the disadvantage that expensive pressurized devices are required, and that, after reaction and addition of water, an aqueous phase containing sodium chloride, alcohol and reaction products is obtained which must be worked up by means of repeated extraction.

Furthermore, a grave drawback of the process in German Pat. No. 2,941,211 is the insufficient purity of the thus-obtained cyclopropanecarboxylic acid esters, the chlorine content of these esters being generally 100 to 1,000 ppm or higher. Due to these high chlorine contents, these esters cannot be catalytically hydrogenated to obtain cyclopropylcarbinol.

In addition, the reactors would be subject to corrosion, and the hydrogenation catalyst would be poisoned. The chlorine content of the esters intended for catalytic hydrogenations must be below 10 ppm.

Therefore, only expensive reagents, such as lithium aluminum hydride, are suitable for the reduction of the chlorine-containing cyclopropanecarboxylic acid esters.

Also, all of the conventional methods require expensive chemicals, pressurized apparatus, and lead to problems with waste disposal. Thus, a process is desired wherein gamma-butyrolactone would be converted in a single-step process into a gamma-chlorobutyric acid ester by reaction with hydrogen chloride and an alcohol, and this product could be cyclized without excess pressure. It would be also desirable for the chlorine content of the product to be sufficiently low that the thus-formed cyclopropanecarboxylic acid ester could be hydrogenated catalytically, for example, to obtain cyclopropylmethanol.

SUMMARY OF THE INVENTION

An object of this invention is to provide a process of this type making it possible with low industrial expenditure and without the use of expensive reagents, to produce, from gamma-butyrolactone, esters of cyclopropanecarboxylic acid and, from these, optionally, cyclopropylcarbinol. These products are well known important raw materials for pharmaceutical products.

A further object is to produce a distilled alkyl ester of cyclopropanecarboxylic acid having a low chlorine content of about not more than 10 ppm, so that there is no need for further purification.

Another object of this invention is to provide a process such that cyclization and interesterification can be performed in one step by adding, during cyclization, the higher-boiling alcohol of more than 4 carbon atoms while removing butanol by distillation. The thus-formed sodium chloride can be readily removed by a water washing step, and the thus-formed wastewater, which has a very low carbon content due to the low water solubility of the higher alcohols employed does not need to be processed.

Still another object is to provide processes for producing intermediates in the process as well as specific single step processes to produce same as well as for reacting such intermediates into desired products.

Upon further study of the specification and appended claims, further objects and advantages of this invention will become apparent to those skilled in the art.

These objects have been achieved by providing a process for producing chlorine-free cyclopropanecarboxylic acid esters through a process of comprising one or more of the following steps:

adding hydrogen chloride and butanol to gamma-butyrolactone, and conducting the reaction essentially free of a catalyst, preferably at a temperature of about 120° C.–140° C., while preferably removing low-boiling compounds (a yield above 95% is obtained), to produce gamma-chlorobutyric acid ester, cyclizing the gamma-chlorobutyric acid butyl ester by adding, at relatively high temperature, the ester to a solution of a sodium alcoholate in corresponding alcohol of four or more carbon atoms (yielding about 95%), and interesterifying the butyl ester with a higher-boiling alcohol of more than four carbon atoms, preferably 5–10 carbon atoms.

In the preparation of gamma-chlorobutyric acid n-butyl ester, the reaction is conducted in an essentially free catalyst milieu. By "essentially free" is meant that insufficient catalyst is present to destroy the advantages of this invention, e.g., not more than 0.1%, preferably not more than 0.001% by weight of catalyst, based on the weight of the starting material. Preferably no catalyst is employed. The reason for this is that in addition to the reducing of costs of catalysts the working up is easier. At the reaction-temperature of about 120° C.–140 ° C. the reaction-water water is removed by distillation.

Gamma-butyrolactone and butanol are provided in a molar ratio of about 1:0.5 to 1:5, preferably 1:1 to 1:2, and heated to boiling under reflux. Suitable butanols include n-butanol, iso-butanol and tert-butanol; n-butanol is preferred. Hydrogen chloride gas is then introduced continuously as the gas is absorbed. In a fractionation column, low-boiling compounds, such as alkyl chlorides, n-butanol and water, are continuously removed by distillation. These compounds generally have a boiling point of about not higher than 11° C. and are removed because the reaction-water must be carried out azeotropically.

The n-butanol discharged is continuously replaced by fresh n-butanol so that the molar ratio of gamma-butyrolactone to n-butanol remains essentially constant, e.g., does not vary more than about 1:0,01 to 1:1, preferably not more than 1:05 to 1:1. By fresh n-butanol is meant dry-butanol. Distilled butanol can be used, if dry.

The molar ratio of gamma-butyrolactone and butanol is kept essentially constant because enough butanol is present for the reaction. But the molar ratio is not critical.

The required reaction temperature is 120°–140° C. When the reaction temperature is outside this range, the reaction is too slow by lower reaction temperature. By higher reaction temperatures too much by products are built.

The preferred temperature range is 126°–136° C.

Cyclization of the gamma-chlorobutyric acid n-butyl ester takes place at about 100°–200° C., preferably 120°–140° C., by providing a solution of sodium alcoholate in alcohol adding the gamma-chlorobutyric acid n-butyl ester, and heating the mixture to boiling under reflux. The preferred alcohols are butanols, especially n-butanol. The preferred sodium alcoholate is sodium n-butylate. During this procedure, the boiling temperature drops from high temperatures proportional to the alcoholate concentration to lower temperatures, for example from 138° to 122° C. The molar ratio of alcoholate to gamma-chlorobutyric acid n-butyl ester is about 1:1 to 1.5:1, preferably 1.1:1 to 1.2:1.

The excess alcoholate serves as a catalyst during the optional step directly following interesterification. In this step, the higher-boiling alcohol is added approximately at the same rate that the n-butanol is removed by distillation. This is because of reducing reactor-volume.

The temperatures in the reactor for cyclization are determined by the boiling point of the alcohol added and range from about 100° to 200° C. This temperature range is desirable because the reaction is too slow by lower reaction temperatures. By higher reaction temperatures too much by-products are built and therefore the yield becomes lower. The molar ratio of cyclopropanecarboxylic acid butyl ester to the higher-boiling alcohol is about 1:1 to 1:5, preferably 1:1.1 to 1:3.

One example of how the thus-obtained cyclopropanecarboxylic acid ester is utilized, is the production of hydroxymethylcyclopropane (cyclopropylmethanol) by hydrogenation. Hydroxymethylcyclopropane is an important intermediate for the manufacture of pharmaceutical products. Hydrogenation is preferably carried out in the sump phase and trickling phase in the presence of a zinc chromite catalyst at 200°–350° C. and under a hydrogen pressure of 200–320 bar. For further details of the hydrogenation reaction and for uses of the hydroxymethylcyclopropane as a starting material for pharmaceuticals, attention is invited to German patent application No. P 35 38 13 and "Pharmazeutische Wirkstoffe" by A. Kleemann and J. Engel, Georg Thieme Verlag, Stuttgart, New York, 1982, p. 619 and 747. Other uses of cyclopropanecarboxylic acid esters include, e.g., the ethylester, see the same literature, page 727.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the preceding text and the following examples, all temperatures are set forth uncorrected in degrees Celsius and all parts and percentages are by weight, unless otherwise indicated.

EXAMPLE 1

(a) Gamma-chlorobutyric Acid n-Butyl Ester (First Step)

A glass apparatus is utilized consisting of a three-necked flask with gas feed pipe, stirrer, thermometer, dropping funnel, and a glass column having a length of 0.5 m and filled with glass Raschig rings, with a distillation attachment.

Starting material:
444 g (6 moles) n-butanol
352 g (4 moles) gamma-butyrolactone (97.7% strength)

The mixture is heated to boiling under reflux, and hydrogen chloride—16 1/h—is immediately introduced. After one-half hour, removal of low-boiling compounds is begun. The course of the synthesis can beseen in Table I.

TABLE I

| Time After Start-up (h) | Temperatures Sump (°C.) | Temperatures Head (°C.) | Ratio Reflux to Discharge | Amount of HCl (l/h) | Feed of n-Butanol in Total (ml) | Distillate Obtained in Total (ml) |
|---|---|---|---|---|---|---|
| Start-Up | 132 | 98 | — | — | — | — |
| 0.5 | 132 | 98 | 5:1 | 16 | — | 20 |
| 1 | 132 | 102 | 5:1 | 16 | — | 45 |
| 1.5 | 132 | 94 | 10:1 | 16 | — | 65 |
| 2–3 | 130 | 93 | 20:1 | 16 | — | 80–120 |
| 3.5–5.5 | 128–126 | 102 | 20:1 | 16 | — | 135–190 |
| 6 | 128 | 102 | 20:1 | 8 | — | 200 |
| 6.5–7.5 | 128–136 | 102 | 20:1 | 8 | 50–90 | 215–250 |
| 8–12 | 136 | 102 | 20:1 | 8 | 110–250 | 260–325 |
| 12.5–15 | 136 | 102 | 20:1 | 8 | 280–420 | 330–395 |
| 15.5 | 136 | 117 | 3:1 | — | — | 405 |
| 16 | 136 | 110 | 3:1 | — | — | 440 |

The addition of n-butanol is regulated so that the sump temperature does not drop.

Analyses by gas chromatography conducted on samples from the sump after 12–16 hours show the following contents of known compounds:

| Compound: | Sample After 12 Hours | Sample After 16 Hours |
|---|---|---|
| n-Butyl Chloride | 0.3% | 0.5% |
| n-Butanol | 23.2% | 24.8% |
| Gamma-butyrolactone | 0.8% | 0.1% |
| Chlorine Ester | 72.0% | 72.0% |

The conversion of gamma-butyrolactone thus ranges, after 16 hours, at 99.9%.

The distillate (387 g), obtained during the reaction and having an acid number of 275.8, is neutralized with 160 g of 50% strength sodium hydroxide solution, and 100 g of water is added to improve separation.

Amount of wastewater: 386 g (C content: 0.38%).

The oil phase (248 g) contains the following known compounds as per analysis by gas chromatography:

| n-Butyl Chloride | 14.7% |
|---|---|
| n-Butanol | 83.4% |
| Lactone | smaller than 0.1% |
| Chlorine Ester | smaller than 0.1% |

During the reaction, 966 g is obtained as the sump product. From this number, and the aforementioned contents, a yield of gamma-chlorobutyric acid n-butyl ester is calculated of 97.3%, based on starting material.

Distillation for obtaining the pure product yields, in a boiling range from 93° to 101° C. under 13 mbar, the gamma-chlorobutyric acid n-butyl ester in a purity of 99.0%. The yield of distilled ester is 93% of theory, based on starting material.

(b) Cyclopropanecarboxylic Acid N-Butyl Ester (Second Step)

A glass apparatus is employed consisting of a three-necked flask with stirrer, thermometer, reflux condenser, and dropping funnel.

Starting material:
718 g of a solution of sodium n-butylate in n-butanol with 2.2 moles of Na n-butylate At 138° C., 361 g (2.0 moles) of gamma-chlorobutyric acid n-butyl ester (First Step Product) is added dropwise within 2 hours under refluxing. During this step, the temperature drops uniformly to 122° C. After the dropwise addition, the mixture is agitated for another hours at 122° C. After cooling, the mixture is washed with water. The carbon content of the wastewater is 0.9%.

Processing by distillation yields, in a boiling range from 111° to 112° C., at 133 mbar, the n-butyl ester of cyclopropanecarboxylic acid in 99.5% purity; its chlorine content is 10 ppm. The yield of distilled ester amounts to 268 g=95% of theory based on starting material.

(c) Interesterification (Third Step) (Optional)

A glass apparatus is utilized consisting of a three-necked flask with stirrer, thermometer, and a glass column having a length of 0.5 m and filled with glass Raschig rings, carrying a distillation attachment.

Starting materials

| 286 g (= 2.0 moles) | of cyclopropanecarboxylic acid n-butyl ester |
|---|---|
| 325 g (= 2.5 moles) | of 2-ethylhexanol |
| 1.6 g (0.9 mole) | of concentrated sulfuric acid |

The low-boiling compounds formed (152 g) are first removed by distillation via the column under normal pressure and at heat temperatures of 93°–117° C. and furthermore under 133 m bar and at head temperatures of 66°–84° C.

After cooling, 2.8 g of 50% sodium hydroxide solution is added to the sump product for neutralizing the sulfuric acid, and distillation is continued under 13 m bar. At a boiling point of 114° C. (under 13 m bar), 360 g of cyclopropanecarboxylic acid 2-ethylhexyl ester is obtained with 98% purity, having a chlorine content of merely 6 ppm. The yield accordingly is 91% of theory based on starting material.

COMPARATIVE EXAMPLE A

The process is conducted as described in Example 1 of German Pat. No. 2,941,211 using a 5-liter stirred autoclave and employing the products mentioned in this example in the indicated quantities. After processing and distillation, 852 g of cyclopropanecarboxylic acid methyl ester is obtained in a boiling range from 14° to 116° C. under normal pressure, i.e., the yield is 94.7% and thus is almost the same as listed in this German patent. The chlorine content of the distilled cyclopropanecrboxylic acid methyl ester is 8,000 ppm. Therefore, this ester cannot be utilized in a catalytic hydrogenation.

EXAMPLE 2

(Cyclization and Interestification in a Single Stage)

The n-butyl ester of gamma-chlorobutyric acid is prepared according to the instructions of Exmaple 1a.

The glass apparatus described in Example 1c is utilized, and the starting material is:

718 g of a solution of sodium 2-ethylhexylate (2.2 moles) in 2-ethylhexanol;

the solution is heated under agitation to 130° C. Then within 4 hours, 360 g = 2 moles of gamma-chlorobutyric acid n-butyl ester is added. After the adding step, the temperature is raised to 160°–164° C., whereupon refluxing occurs, and the mixture is further stirred for 2 hours at this temperature range.

Subsequently, butanol is distilled off at the column, increasing the sump temperature thereby to about 200° C.

After cooling, the mixture is washed twice with water, first with 400 g and then 200 g. The carbon content of the wastewater from the first washing step (512 g) is 1.5%, and of the wastewater from the second washing step (212 g) is 1.2%. Processing by distillation yields, in a boiling range from 113° to 114° C. under 113 m bar, the 2-ethylhexyl ester of cyclopropanecarboxylic acid in a purity of 99.1% with a chlorine content of merely 6 ppm. The yield of distillate, 357 g, corresponds to a yield of about 90% based on the gamma-chlorobutyric acid n-butyl ester utilized.

What is claimed is:

1. In a process for the production of cyclopropanecarboxylic acid esters by reacting gamma-butyrolactone with an alcohol and gaseous hydrogen chloride to obtain the gamma-chlorobutyric acid ester and cyclization of the latter with an alkali alcoholate to obtain the cyclopropanecarboxylic acid ester, the improvement comprising:

(a) reacting gamma-butyrolactone and butanol in a reaction mixture essentially free of a catlyst with hydrogen chloride while removing, via a column, low-boiling compounds and water by distillation, whereby said esters are essentially free of chloride compounds resulting from conducting said process.

2. A process of claim 1, wherein the reaction is carried out at a temperature of 120°–140° C.

3. A process of claim 1, wherein the reaction is carried out at a temperature of 126°–136° C.

4. A process of claim 2, wherein the molar ratio of gamma-butyrolactone to butanol is about 1:0.5 to 1:5.

5. A process of claim 3, wherein the gamma-butylactone and butanol are in a molar ratio of about 1:1 to 1:2.

6. A process of claim 4, further comprising continuously replacing the discharged butanol with fresh butanol so that the molar ratio of gamma-butyrolactone to butanol remains essentially constant.

7. A process of claim 1, further comprising (b) cyclizing the gamma-chlorobutyric acid butyl ester obtained in (a) with a solution of a sodium alcoholate in the corresponding alcohol of at least 4 carbon atoms, at about 100°–200° C., and a molar ratio of alcoholate to gamma-chlorobutyric acid butyl ester of about 1:1 to 1.5:1.

8. A process of claim 7, wherein the molar ratio of alcoholate to gamma-chlorobutyric acid butyl ester in step (b) is about 1.1: to 1.2:1.

9. A process of claim 7, wherein the reaction of step (b) is carried out at about 120°–140° C.

10. A process of claim 7, wherein the sodium alcoholate in step (b) is sodium n-butylate.

11. A process of claim 7, wherein the higher alcohol in step (b) has 5–20 carbon atoms, preferably 5–10 and the resultant n-butanol is removed by distillation.

12. A process of claim 7, further comprising:

(c) interesterfying the cyclopropanecarboxylic acid ester obtained in step (b) with a higher-boiling alcohol of more than 4 carbon atoms, at a temperature of 120°–200° C.

13. A process of claim 12, wherein the alcohol in step (c) has 5–10 carbons atoms.

14. a process of claim 12, wherein steps (b) and (c) are performed simultaneously.

15. A process for the production of pure gamma-chlorobutyric acid ester, comprising:

reacting gamma-butyrolactone and butanol, essentially free of catalyst, at 120°–140° C.

16. In a process for the production of cyclopropanecarboxylic acid esters the improvement comprising:

cyclizing gamma-chlorobutyric acid butyl ester with a solution of a sodium alcoholate in the corresponding alcohol of at least 4 carbon atoms, at about 100°–200° C., and molar ratio of alcoholate to gamma-chlorobutyric acid butyl ester of about 1:1 to 1.5:1; said gamma-chlorobutyric acid butyl ester being the product of reacting gamma-butyrolactone and butanol, essentially free of a catalyst, with hydrogen chloride while removing, via a column, low-boiling compounds and water by distillation, whereby said esters are essentially free of chloride compounds resulting from conducting said process.

17. A process of claim 13 further comprising: interesterifying the cyclopropanecarboxylic acid ester with a higher-boiling alcohol of more than 4 carbon atoms, at temperatures of 120°–200° C.

18. A process according to claim 15 conducted in the complete absence of a catalyst.

* * * * *